United States Patent [19]

Jones et al.

[11] 4,442,127
[45] * Apr. 10, 1984

[54] NAPHTHOQUINONE ANTI-PSORIATIC AGENTS

[75] Inventors: Gordon H. Jones, Cupertino; John M. Young, Redwood City, both of Calif.

[73] Assignee: Syntex (U.S.A.) Inc., Palo Alto, Calif.

[*] Notice: The portion of the term of this patent subsequent to Oct. 21, 1997 has been disclaimed.

[21] Appl. No.: 459,165

[22] Filed: Jan. 19, 1983

Related U.S. Application Data

[60] Continuation-in-part of Ser. No. 255,624, Apr. 20, 1981, abandoned, which is a continuation of Ser. No. 144,479, Apr. 28, 1980, abandoned, which is a division of Ser. No. 912,697, Jun. 5, 1978, Pat. No. 4,229,478.

[51] Int. Cl.³ .................. A61K 31/12; A61K 31/275; C07C 50/00; C07C 97/18
[52] U.S. Cl. ............................. 424/331; 260/396 R; 424/304
[58] Field of Search ............................. 424/331, 304; 260/396 R

[56] References Cited

U.S. PATENT DOCUMENTS 3,914,264 10/1975 Marsico et al. ................ 260/396 R
4,229,478 10/1980 Jones et al. ........................ 424/331

OTHER PUBLICATIONS

Chemical Abstracts 38:3278 (1944).
Chemical Abstracts 42:7750 (1978).
Chemical Abstracts 52:12011b (1958).

*Primary Examiner*—Leonard Schenkman
*Attorney, Agent, or Firm*—Annette M. Moore; Tom M. Moran

[57] ABSTRACT

Psoriasis in mammals is relieved by topically administering naphthoquinones of the formula:

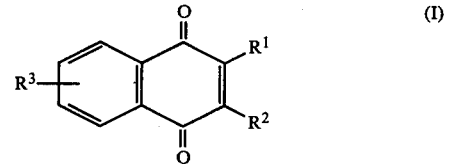

wherein:
  $R^1$ and $R^2$ are lower alkoxy; and
  $R^3$ is halo or cyano.

14 Claims, No Drawings

NAPHTHOQUINONE ANTI-PSORIATIC AGENTS

BACKGROUND OF THE INVENTION

This is a continuation-in-part of U.S. Ser. No. 255,624 filed Apr. 20, 1981 now abandoned which is a continuation of U.S. Ser. No. 144,479 filed Apr. 28, 1980 now abandoned, which is a division of U.S. Ser. No. 912,697 filed June 5, 1978, now U.S. Pat. No. 4,229,478.

FIELD OF THE INVENTION

The invention relates to naphthoquinone derivatives which are useful in inhibiting certain dermatological conditions. This invention also relates to pharmaceutical compositions useful in relieving the effects of certain chronic recurrent papulosquamous dermatoses, e.g., psoriasis. This invention also relates to a process for preparing compounds of this invention.

RELATED DISCLOSURES

Psoriasis is a skin disease characterized in part by excessive proliferation of cells of the epidermis which remain strongly adherent and build up into a scaley plaque typical of the disease. Currently available therapies, which are not curative, depend on the control of epidermal cell proliferation through the use of hormonal agents, such as corticosteroids or through the use of compounds related to cancer chemotherapy such as hydroxyurea, methotrexate, and the nitrogen mustards.

While the above agents are effective to a certain extent, they cause numerous severe undesirable side effects including renal irritation, hepatic toxicity, and erythema.

Certain substituted naphthoquinones are known. See, for example, Ber. 76B, 924-36, 1943; Chem. Ber. 80, 391-401, 1947; and German Patent No. 859,008. No useful biological activity has been ascribed to these compounds. It has been found that the compounds of the instant invention are useful in treating psoriasis.

SUMMARY

The present invention relates to a pharmaceutical composition in a form suitable for topical administration to mammals comprising a compound of the following formula $$\text{(I)}$$

wherein:
$R^1$ and $R^2$ are lower alkoxy of one to six carbon atoms; and
$R^3$ is halo or cyano.

Another aspect of the invention is a method for relieving the condition of psoriasis in a mammal which comprises topically administering to said mammal a psoriasis-relieving amount of a compound of formula (I).

Another aspect of the invention is the novel compounds of formula (I) wherein $R^1$, $R^2$ and $R^3$ are as defined above.

Yet another aspect of the invention is preparing compounds of formula (I).

DETAILED DESCRIPTION AND PREFERRED EMBODIMENT

In its broadest aspect, the present invention relates to a pharmaceutical composition in a form suitable for topical administration to mammals comprising a compound of the following formula $$\text{(I)}$$

wherein:
$R^1$ and $R^2$ are lower alkoxy of one to six carbon atoms; and
$R^3$ is halo or cyano.

The present invention also relates to compounds of the formula $$\text{(I)}$$

wherein:
$R^1$ and $R^2$ are lower alkoxy of one to six carbon atoms; and
$R^3$ is halo or cyano.

More specifically, the present invention relates to compositions containing compounds of formula (I) wherein $R^3$ is in the 6-position and is bromo, chloro, fluoro or cyano.

An even more specific embodiment of the instant invention are compounds of formula (I) wherein $R^3$ is at the 6-position and is bromo, chloro, fluoro, or cyano.

Within this specific embodiment of the instant invention, a preferred group of compounds of formula (I) are those wherein $R^1$ and $R^2$ are lower alkoxy of one to three carbon atoms and $R^3$ is in the 6-position and is chloro.

The term "lower alkoxy" refers to a straight or branched chain aliphatic group of one to six carbon atoms having bonded thereto an oxygen moiety. Examples of "lower alkoxy" are methoxy, ethoxy, n-propoxy, i-propoxy, n-butoxy, i-butoxy, s-butoxy, t-butoxy, n-pentyloxy and n-hexyloxy.

The term "halo" refers to fluoro, chloro, and bromo.
The term "cyano" refers to the group —CN.

FORMULATION AND ADMINISTRATION

The compositions of the present invention may be formulated for administration in any convenient way by analogy with other topical compositions adapted for use in mammals. These compositions may be presented for use in any conventional manner with the aid of any of a wide variety of pharmaceutical carriers or vehicles.

The naphthoquinones of formula (I) may be formulated with suitable pharmaceutical vehicles known in the art to form particularly effective topical compositions. An effective amount of the naphthoquinone compound is about 0.001%w to about 10%w of the total formulated composition. The rest of the formulated composition will be about 90%w to about 99.999%w of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the naphthoquinones therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

| Water/glycol mixture (15% or more glycol) | 50-99 parts by weight |
|---|---|
| Fatty Alcohol | 1-20 |
| Non-ionic Surfactant | 0-10 |
| Mineral Oil | 0-10 |
| Typical Pharmaceutical Adjuvants | 0-5 |
| Active Ingredients | 0.001-10 |

The fatty alcohol, non-ionic surfactant, and other adjuvants are discussed in U.S. Pat. No. 3,934,013 to Poulsen which is incorporated herein by reference.

The naphthoquinones of formula (I) may also be formulated as topical ointments. A "classical" ointment is a semisolid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| White Petrolatum | 40-94 parts by weight |
|---|---|
| Mineral Oil | 5-20 |
| Glycol Solvent | 1-15 |
| Surfactant | 0-10 |
| Stabilizer | 0-10 |
| Active Ingredients | 0.001-10.0 |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| Active Ingredients | 0.001-10.0 parts by weight |
|---|---|
| Propylene Carbonate | 1-10 |
| Solvent | 1-10 |
| Surfactant | 0-10 |
| White Petrolatum | 70-97 |

Suitable solvents, surfactants, stabilizers, etc. are discussed in U.S. Pat. No. 3,934,013 and such are incorporated herein by reference.

A suitable topical "non-classical" anhydrous, water washable "ointment type" base is described in U.S. Pat. No. 3,592,930 to Katz and Neiman, and that patent is incorporated herein by reference. A representative composition of this invention utilizing such base is as follows:

| Glycol Solvent | 40-35 parts by weight |
|---|---|
| Fatty Alcohol | 15-45 |
| Compatible Plasticizer | 0-15 |
| Compatible Coupling Agent | 0-15 |
| Penetrant | 0-20 |
| Active Ingredients | 0.001-10.0 |

Another aspect of the invention is a method for relieving the condition of psoriasis in a mammal by topically administering a composition containing a compound of formula (I). Generally, the anti-psoriatic manifestation in mammals, particularly humans, is combatted by contacting the inflamed areas with a therapeutically effective amount of the naphthoquinone-containing compositions of this invention, that is, an amount which results in a lessening of the epidermal cell proliferation (an anti-psoriatic effect). Preferably the naphthoquinones are first formulated to prepare a suitable pharmaceutical formulation, as discussed hereinabove, which is then placed in contact with the afflicted area(s). An effective amount of the naphthoquinone compound will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to affect an anti-psoriatic response, but not enough to adversely effect the recipient, is applied to the afflected area(s).

PREPARATION

The compounds of formula (I) may be prepared by the reaction sequences below.

Reaction Sequence I

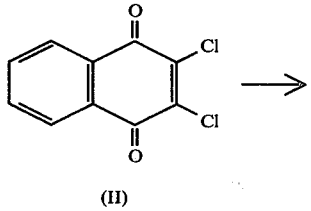

(II)

-continued
Reaction Sequence I

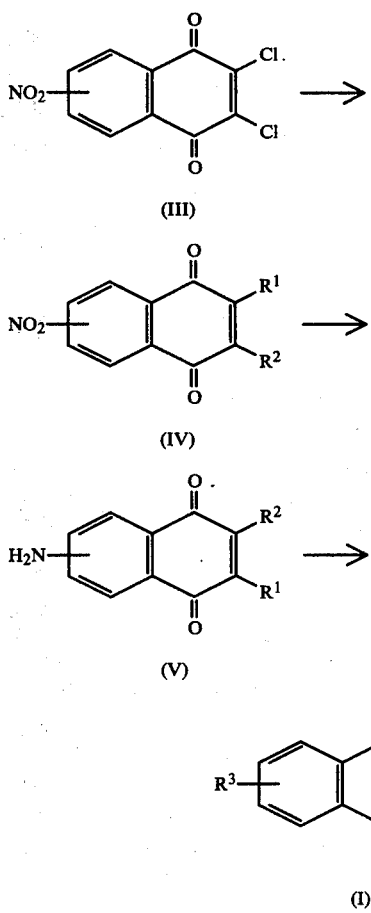

wherein $R^1$, $R^2$, and $R^3$ are as defined above.

Compounds of formula (III) are prepared by starting with a 2,3-dihalonaphthoquinone, preferably 2,3-dichloro-1,4-naphthoquinone (compound of formula (II)), which is available from, i.a., Aldrich Chemical Co., and directly nitrating. The reaction proceeds in the manner known for polycyclic aromatic compounds to yield a mixture of the 5- and 6-nitro-2,3-dichloro-1,4-napthoquinones, compounds of formula (III). The reaction is conducted typically with concentrated nitric acid in a low pH solvent medium, preferably concentrated sulfuric acid, typically at 20° C. to 100° C. for a time sufficient to complete the reaction. Depending on the reaction temperature and times of reaction, ratios of the 5-nitro isomer:6-nitro isomer mixture may range from 10:1 to 1:10, typically 8:1.

Compounds of formula (IV) are synthesized from 5- and 6-nitro-2,3-dichloro-1,4-naphthoquinone, compound of formula (III), by condensing them with an alkali metal alkoxide, wherein the alkoxy moiety is $R^1=R^2$. The reaction is preferably conducted in an inert organic solvent such as tetrahydrofuran, dimethylsulfoxide, dimethylformamide and the like at temperatures from about 20° C. to about 100° C. for a time sufficient to assure completeness of reaction, i.e., for about 2 hours to about 48 hours.

The compounds of formula (V) are prepared from compounds of formula (IV) by catalytic or non-catalytic reduction processes known in the prior art. Metal-acid reducing agent compositions, such as granulated iron and hydrochloric acid, tin and hydrochloric acid, and the like or neutral reducing agent compositions such as zinc dust and aqueous alcohol or aluminum amalgam and aqueous alcohol as well as organo-metallic reducing agents such as lithium aluminum hydride, sodium borohydride and the like may be used in this reduction. Preferably, the reduction is accomplished by treating the compounds of formula (IV) with excess hydrazine in the presence of a catalytically sufficient amount of palladium, typically on carbon. The reaction readily occurs at room temperature, the time of reaction being governed by the rate of addition of the hydrazine to the reaction mixture such typically being about 1 to about 10 hours.

Compounds of formula (V) are converted into compounds of formula (I) where $R^3$ is halo by adding to the compound of formula (V) in an acidified aqueous solution, a solution of an alkali metal nitrite. This initial reaction forms the diazonium salt at the 5- or 6-position of the naphthoquinone ring. The salt is decomposed with a solution of cuprous halide dispersed or dissolved in the corresponding halogen acid (the Sandmeyer reaction). This classical reaction is treated extensively in Bigelow, Org. Synthesis, Coll. Vol. I, 126-133 (1941).

A modification of the above Sandmeyer reaction is useful in the preparation of the compounds of formula (I) where $R^3$ is cyano in that the diazonium salt, rather than being decomposed in the presence of cuprous halide/halogen acid is decomposed in the presence of an alkali metal cyanide and a cuprous halide. See Clarke and Read, Org. Synthesis, Coll. Vol. I, 514 (1941) for a further explanation of the considerations involved in this modified Sandmeyer reaction.

A particularly preferred method of preparing compounds of formula (I) wherein $R^3$ is 6-halo is shown in the following reaction sequence.

REACTION SEQUENCE II

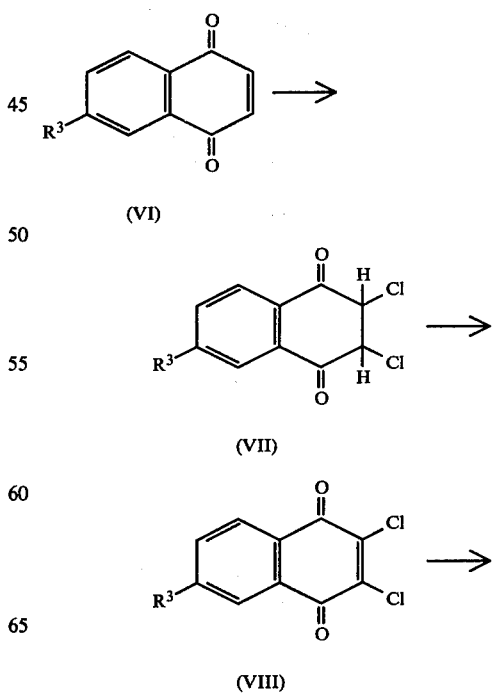

-continued
REACTION SEQUENCE II

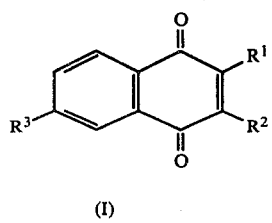

(I)

wherein $R^1$ and $R^2$ are as defined above.

Compounds of formula (VI) are prepared according to the method disclosed in J. Am. Chem. Soc., 70, 3165 (1948) and Ibid., 71, 3615 (1949). Halo substituted butadiene is reacted with 1,4-benzoquinone in a solvent such as acetic acid at a temperature of $-10°$ C. to 30° C., preferably at 25° C. for 24 to 72 hours, preferably from 40 to 48 hours. The 5,7-dihydro compound of formula (VI) is recovered and treated with an oxidizing agent such as sodium dichromate, sodium nitrite and the like as described in the above articles to form compounds of formula (VI). Compounds of formula (VII) are prepared by bubbling chlorine gas into a solution of compound of formula (VI) dissolved in a solvent such as glacial acetic acid, nitrobenzene, carbon tetrachloride and the like, preferably glacial acetic acid at room temperature. This compound, which may be isolated by known means, dissolved in a solvent such as acetic acid is treated with chlorine gas and a suitable catalyst such as sodium acetate, iodine, iron(III)chloride, dimethylformamide or alcohols with heating under reflux for $\frac{1}{2}$ to 4 hours, preferably for 1 to $2\frac{1}{2}$ hours to yield compounds of formula (VIII). Compounds of formula (I) wherein $R^3$ is halo are prepared by reacting compound of formula (VIII) with an alkali metal alkoxide such as sodium alkoxide, e.g., sodium methoxide in an anhydrous solvent such as methanol, dimethylformamide and the like, the solvent being chosen according to the length of the alkyl chain on the alkoxy group. The reaction mixture is heated under reflux for $\frac{1}{2}$ to 3 hours, preferably for $\frac{1}{2}$ to $1\frac{1}{2}$ hours. Compounds of formula (I) are recovered by conventional means such as by crystallization.

The intermediate, 2-chloro-1,3-butadiene (chloroprene) is available from, i.a., Pfaltz and Bauer Chemical Co. 2-Bromo-1,3-butadiene and 2-fluoro-1,3-butadiene may be prepared by methods well known in the art, for example, by the methods discussed in J. Am. Chem. Soc., 55, 786 (1933) and U.S. Pat. No. 2,401,850, respectively.

The following specific description is given to enable those skilled in the art to more clearly understand and practice the present invention. It should not be considered as a limitation upon the scope of the invention but merely as illustrative and representative thereof.

PREPARATION 1

2,3-Dichloro-5- and 6-nitro-1,4-naphthoquinone (Preparation of Compounds of Formula (III))

Finely powdered 2,3-dichloro-1,4-naphthoquinone 50 g. 0.22 mol) was added to a stirred mixture of concentrated sulfuric acid (170 ml) and 90% nitric acid (102 ml) at a rate so that the exothermic reaction raised the temperature to 60° C. The resulting mixture was stirred at 60° C. for a further 2 hours. The yellow crystalline solid was filtered off, washed thoroughly with water and recrystallized from chloroform giving 22.9 g of the 5-nitro isomer, mp 156°–157° C. The above strongly acidic filtrate was poured onto ice water. The resultant solid was filtered off, washed thoroughly with water and dried giving 20.8 g of a mixture of the 5- and 6-isomer. Fractional crystallization of this mixture from acetic acid and chloroform:isopropanol afforded 2.8 g of the 6-nitro isomer, mp 184°–187° C.

Further quantities of both 5- and 6-isomer were obtained from the recrystallization mother liquors by chromatography on a silica gel column eluting with chloroform:cyclohexane mixtures.

PREPARATION 2

2,3-Dimethoxy-5-nitro-1,4-naphthoquinone (Preparation of Compounds of Formula (IV))

A. A solution of 2,3-dichloro-5-nitro-1,4-naphthoquinone (2.72 g, 10 mmol) in anhydrous tetrahydrofuran (15 ml) was added to a solution of 1 N sodium methoxide (25 ml, 25 mmol) and the resulting solution stored at 22° for 16 hours. Acetic acid (1 ml) was then added, the solution concentrated in vacuo and the residue partitioned between water (50 ml) and chloroform (100 ml). The aqueous phase was further extracted with chloroform (2×50 ml). The combined chloroform extracts were dried with $MgSO_4$ and concentrated in vacuo. The residue was recrystallized from methanol giving 1.99 g of 2,3-dimethoxy-5-nitro-1,4-naphthoquinone, mp 156°–157°.

B. Similarly, using the above procedure in Part A, substituting 2,3-dichloro-6-nitro-1,4-naphthoquinone, where appropriate, for 2,3-dichloro-5-nitro-1,4-naphthoquinone and the appropriate sodium alkoxide for sodium methoxide, the following compounds are prepared:

2,3-dimethoxy-6-nitro-1,4-naphthoquinone, mp 113°–114° C.;
2,3-diethoxy-5-nitro-1,4-naphthoquinone;
2,3-diethoxy-6-nitro-1,4-naphthoquinone;
2,3-di-n-propoxy-5-nitro-1,4-naphthoquinone;
2,3-di-n-propoxy-6-nitro-1,4-naphthoquinone;
2,3-di-i-propoxy-5-nitro-1,4-naphthoquinone;
2,3-di-i-propoxy-6-nitro-1,4-naphthoquinone;
2,3-di-n-butoxy-5-nitro-1,4-naphthoquinone;
2,3-di-n-butoxy-6-nitro-1,4-naphthoquinone;
2,3-di-s-butoxy-5-nitro-1,4-naphthoquinone;
2,3-di-s-butoxy-6-nitro-1,4-naphthoquinone;
2,3-di-n-pentyloxy-5-nitro-1,4-naphthoquinone;
2,3-di-n-pentyloxy-6-nitro-1,4-naphthoquinone;
2,3-di-s-pentyloxy-5-nitro-1,4-naphthoquinone;
2,3-di-s-pentyloxy-6-nitro-1,4-naphthoquinone;
2,3-di-n-hexyloxy-5-nitro-1,4-naphthoquinone;
2,3-di-n-hexyloxy-6-nitro-1,4-naphthoquinone;
2,3-di-i-hexyloxy-5-nitro-1,4-naphthoquinone;
2,3-di-i-hexyloxy-6-nitro-1,4-naphthoquinone;
2,3-di(2,2-dimethylpropoxy)-5-nitro-1,4-naphthoquinone; and
2,3-di(2,2-dimethylpropoxy)-6-nitro-1,4-naphthoquinone.

PREPARATION 3

2,3-Dimethoxy-5-amino-1,4-naphthoquinone (Preparation of Compounds of Formula (V))

Hydrazine (4.0 ml, 125 mmol of 97%) was added dropwise, over a 2 hour period, to a stirred mixture of the captioned compound of Preparation 2 (19.9 g, 75.6 mmol), 5% palladium on carbon (10 g) and ethanol (750 ml) in a nitrogen atmosphere. The catalyst was filtered off through a celite pad that was washed with hot ethanol (2×300 ml). The combined filtrate and washings were concentrated to dryness in vacuo and the residue recrystallized from water:ethanol (1.5:1) giving 14.6 g of 2,3-dimethoxy-5-amino-1,4-naphthoquinone, mp 116°–117°.

Similarly, substituting the compounds from Preparation 2 for 2,3-dimethoxy-5-nitro-1,4-naphthoquinone the following compounds are prepared:
2,3-dimethoxy-6-amino-1,4-naphthoquinone, mp 196°–197° C.;
2,3-diethoxy-5-amino-1,4-naphthoquinone;
2,3-diethoxy-6-amino-1,4-naphthoquinone;
2,3-di-n-propoxy-5-amino-1,4-naphthoquinone;
2,3-di-n-propoxy-6-amino-1,4-naphthoquinone;
2,3-di-i-propoxy-5-amino-1,4-naphthoquinone;
2,3-di-i-propoxy-6-amino-1,4-naphthoquinone;
2,3-di-n-butoxy-5-amino-1,4-naphthoquinone;
2,3-di-n-butoxy-6-amino-1,4-naphthoquinone;
2,3-di-s-butoxy-5-amino-1,4-naphthoquinone;
2,3-di-s-butoxy-6-amino-1,4-naphthoquinone;
2,3-di-n-pentyloxy-5-amino-1,4-naphthoquinone;
2,3-di-n-pentyloxy-6-amino-1,4-naphthoquinone;
2,3-di-s-pentyloxy-5-amino-1,4-naphthoquinone;
2,3-di-s-pentyloxy-6-amino-1,4-naphthoquinone;
2,3-di-n-hexyloxy-5-amino-1,4-naphthoquinone;
2,3-di-n-hexyloxy-6-amino-1,4-naphthoquinone;
2,3-di-i-hexyloxy-5-amino-1,4-naphthoquinone;
2,3-di-i-hexyloxy-6-amino-1,4-naphthoquinone;
2,3-di(2,2-dimethylpropoxy)-5-amino-1,4-naphthoquinone; and
2,3-di(2,2-dimethylpropoxy)-6-amino-1,4-naphthoquinone.

EXAMPLE 1

5-Chloro-2,3-dimethoxy-1,4-naphthoquinone (Preparation of Compounds of Formula (I) where $R^3$ is 5-chloro)

A solution of sodium nitrite (0.69 g, 10 mmol) in water (5 ml) was added at 0°–5° C. to a solution of 5-amino-2,3-dimethoxy-1,4-naphthoquinone (1.17 g, 5 mmol) in 5:1 acetic acid:water (25 ml) containing concentrated hydrochloric acid (1.7 ml). A further quantity of sodium nitrite (0.69 g) was then added to the reaction mixture after cooling to −5° C., followed by a solution of cuprous chloride (0.6 g) in concentrated hydrochloric acid (5 ml). The mixture was allowed to warm to 22° C. and solid cuprous chloride was added portionwise until the mixture assumed a green color. Water was then added to the reaction mixture and the precipitated yellow solid filtered off, washed with water and recrystallized from methanol:water (2:1) giving 1.01 g of 5-chloro-2,3-dimethoxy-1,4-naphthoquinone, mp 120°–121° C.

Similarly, proceeding as above substituting the appropriate compounds for 2,3-dimethoxy-5-amino-1,4-naphthoquinone the following compound are prepared:
6-chloro-2,3-dimethoxy-1,4-naphthoquinone;
5-chloro-2,3-diethoxy-1,4-naphthoquinone;
6-chloro-2,3-diethoxy-1,4-naphthoquinone;
5-chloro-2,3-di-n-propoxy-1,4-naphthoquinone;
6-chloro-2,3-di-n-propoxy-1,4-naphthoquinone;
5-chloro-2,3-di-i-propoxy-1,4-naphthoquinone;
6-chloro-2,3-di-i-propoxy-1,4-naphthoquinone;
5-chloro-2,3-di-n-butoxy-1,4-naphthoquinone;
6-chloro-2,3-di-n-butoxy-1,4-naphthoquinone;
5-chloro-2,3-di-s-butoxy-1,4-naphthoquinone;
6-chloro-2,3-di-s-butoxy-1,4-naphthoquinone;
5-chloro-2,3-di-n-pentyloxy-1,4-naphthoquinone;
6-chloro-2,3-di-n-pentyloxy-1,4-naphthoquinone;
5-chloro-2,3-di-s-pentyloxy-1,4-naphthoquinone;
6-chloro-2,3-di-s-pentyloxy-1,4-naphthoquinone;
5-chloro-2,3-di-n-hexyloxy-1,4-naphthoquinone;
6-chloro-2,3-di-n-hexyloxy-1,4-naphthoquinone;
5-chloro-2,3-di-i-hexyloxy-1,4-naphthoquinone;
6-chloro-2,3-di-i-hexyloxy-1,4-naphthoquinone;
5-chloro-2,3-di(2,2-dimethylpropoxy)-1,4-naphthoquinone; and
6-chloro-2,3-di(2,2-dimethylpropoxy)-1,4-naphthoquinone.

EXAMPLE 2

5-Cyano-2,3-dimethoxy-1,4-naphthoquinone (Preparation of Compounds of Formula (I) where $R^3$ is cyano)

A solution of sodium nitrite (2.21 g, 32 mmol) in water (6 ml) was added at 0°–5° C. to a stirred suspension of 5-amino-2,3-dimethoxy-1,4-naphthoquinone (3.73 g, 16 mmol) in 3:1 water:tetrahydrofuran (20 ml) containing concentrated hydrochloric acid (6.7 ml) and the resulting mixture was stirred at 0°–5° C. for a further 1¼ hour. The almost clear solution is then neutralized with sodium carbonate, filtered and added at 5° C. to a vigorously stirred solution of cuprous chloride (4.75 g) and sodium cyanide (5.88 g) in water (80 ml). Ethyl acetate (100 ml) was added and the mixture is heated at 45° C. for 0.5 hours, filtered through a celite bed and separated into the two phases. The aqueous phase was extracted with ethyl acetate (2×100 ml). The combined organic phases were extracted with brine (150 ml), dried over MgSO$_4$ and concentrated to dryness in vacuo. The residue was recrystallized from isopropanol giving 2.96 g of 5-cyano-2,3-dimethoxy-1,4-naphthoquinone, mp 171°–172° C.

Similarly, proceeding as above the following compound is prepared:
6-cyano-2,3-dimethoxy-1,4-naphthoquinone;
6-cyano-2,3-diethoxy-1,4-naphthoquinone;
6-cyano-2,3-di-i-propoxy-1,4-naphthoquinone; and
6-cyano-2,3-di-n-butoxy-1,4-naphthoquinone.

EXAMPLE 3

A. (Preparation of compounds of formula (VIII) wherein $R^3$ is 6-chloro)

Into a solution of 6-chloro-1,4-naphthoquinone (193 g) in glacial acetic acid (1600 mL) was bubbled chlorine gas until TLC of an aliquot showed complete disappearance of 6-chloro-1,4-naphthoquinone. The resulting precipitate was collected by filtration, and washed with acetic acid (200 mL) and hexane (2×300 mL) and air dried to yield the 2,3,6-trichloro-2,3-dihydro-1,4-naphthoquinone (157 g). The solid was transferred into a flask equipped with a mechanical stirrer and reflux condenser. Sodium acetate (98.4 g) and acetic acid (1.5 L) were added, and into the suspension was bubbled chlorine gas. The mixture was brought to reflux and maintained there for 2 hours. The cooled mixture was poured over water (3.5 L), and the resulting precipitate was collected by filtration, and was washed with water (2×500 mL), air dried and then vacuum dried over phosphorus pentoxide, to yield 2,3,6-trichloro-1,4-naphthoquinone (139 g), mp 147.5°–148.5° C.

Similarly, using the above procedure are prepared:
6-bromo-2,3-dichloro-1,4-naphthoquinone; and
6-fluoro-2,3-dichloro-1,4-naphthoquinone.

B. (Preparation of compounds of formula (I) wherein $R^3$ is 6-chloro)

To a mechanically stirred solution of sodium methoxide (55.5 g) in anhydrous methanol (1.5 L) under a blanket of nitrogen was added 2,3,6-trichloro-1,4-naphthoquinone from Preparation 10 (130 g) as rapidly as possible. The temperature rose to 50° C. during the addition, and the reaction was then heated to reflux for 1 hour. The mixture was cooled and acidified with 6 M hydrochloric acid to give a brilliant yellow color. After the addition of water (300 mL), the reaction mixture was filtered, and the precipitate was washed with aqueous methanol (4:1 water-methanol) until the filtrate was yellow-orange. The precipitate was air dried to yield 6-chloro-2,3-dimethoxy-1,4-naphthoquinone (102 g), mp 125°–126° C.

Similarly, using the above procedure, the following compounds are prepared:
6-bromo-2,3-dimethoxy-1,4-naphthoquinone;
6-fluoro-2,3-dimethoxy-1,4-naphthoquinone;
6-chloro-2,3-diethoxy-1,4-naphthoquinone;
6-bromo-2,3-diethoxy-1,4-naphthoquinone; and
6-fluoro-2,3-diethoxy-1,4-naphthoquinone.

EXAMPLE 4

A. To a solution of sodium-n-butoxide (25.8 g) in dry dimethylformamide (125 ml) was added 2,3,6-trichloro-1,4-naphthoquinone (28 g) in one amount. The mixture was refluxed for 2 hours, then cooled, acidified with 6 M hydrochloric acid and evaporated. The residue was chromatographed over silica gel using dichloromethane as eluant to yield 2,3-di-n-butoxy-6-chloro-1,4-naphthoquinone (12.3 g) as a red oily solid.

B. Similarly, proceeding as above in Part A, substituting the appropriate compound for 2,3,6-trichloro-1,4-naphthoquinone and the appropriate sodium alkoxide for sodium-n-butoxide, the following compounds are prepared:
6-chloro-2,3-di-i-butoxy-1,4-naphthoquinone;
6-chloro-2,3-di(2,2-dimethylpropoxy)-1,4-naphthoquinone;
6-chloro-2,3-di-n-propoxy-1,4-naphthoquinone;
6-bromo-2,3-di-n-propoxy-1,4-naphthoquinone;
6-fluoro-2,3-di-n-propoxy-1,4-naphthoquinone;
6-bromo-2,3-di-n-butoxy-1,4-naphthoquinone;
6-fluoro-2,3-di-n-butoxy-1,4-naphthoquinone; and
6-chloro-2,3-di-n-hexyloxy-1,4-naphthoquinone.

What is claimed is:

1. A composition in a form for topical administration to mammals for relieving the condition of psoriasis which comprises a pharmaceutically acceptable, nontoxic carrier and a psoriasis-relieving amount of a compound of the formula

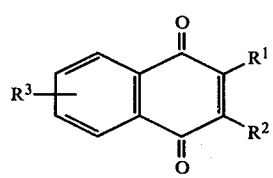

where $R^1$ and $R^2$ are lower alkoxy of one to six carbon atoms and $R^3$ is halo or cyano.

2. The composition according to claim 1 wherein said compound is

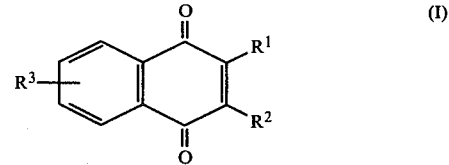

wherein $R^1$ and $R^2$ are lower alkoxy of one to six carbon atoms and $R^3$ is halo or cyano.

3. The composition according to claim 2 where $R^3$ is fluoro, chloro or bromo.

4. The composition according to claim 2 wherein $R^3$ is cyano.

5. A composition of claim 3 wherein said compound is 6-chloro-2,3-dimethoxy-1,4-naphthoquinone.

6. A composition of claim 3 wherein said compound is 6-chloro-2,3-di-n-butoxy-1,4-naphthoquinone.

7. A compound of the formula

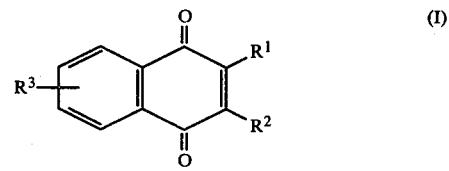

wherein $R^1$ and $R^2$ are lower alkoxy of one to six carbon atoms and $R^3$ is cyano.

8. A compound of the formula

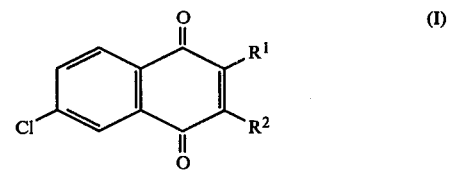

wherein $R^1$ and $R^2$ are lower alkoxy of one to six carbon atoms.

9. A compound of claim 8 which is 6-chloro-2,3-dimethoxy-1,4-naphthoquinone.

10. A compound of claim 8 which is 6-chloro-2,3-di-n-butoxy-1,4-naphthoquinone.

11. A method for relieving the condition of psoriasis which comprises topically administering to mammals in need thereof an effective amount of a compound of the formula

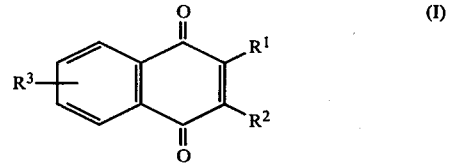

wherein $R^1$ and $R^2$ are lower alkoxy of one to six carbon atoms and $R^3$ is halo or cyano.

12. A method for relieving the condition of psoriasis which comprises topically administering to mammals in need thereof an effective amount of a compound of the formula
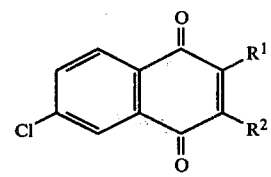
wherein $R^1$ and $R^2$ are lower alkoxy of one to six carbon atoms.
13. A method according to claim 12 wherein $R^1$ and $R^2$ are methoxy.
14. A method according to claim 12 wherein $R^1$ and $R^2$ are n-butoxy.
* * * * *